United States Patent [19]
Khan et al.

[11] Patent Number: 5,582,900
[45] Date of Patent: Dec. 10, 1996

[54] SPIN-TRANSITION COMPOUNDS AND THEIR USE FOR STORING, PROCESSING AND/OR DISPLAYING INFORMATION

[75] Inventors: Olivier O. Khan, Massy; Charlotte Jay, Paris; Jonas Krober, Palaiseau, all of France

[73] Assignee: U.S. Philips Corporation, New York, N.Y.

[21] Appl. No.: 247,383

[22] Filed: May 23, 1994

Related U.S. Application Data

[63] Continuation-in-part of Ser. No. 979,104, Nov. 20, 1992, abandoned.

[30] Foreign Application Priority Data

Nov. 22, 1991 [FR] France ................... 91 14426

[51] Int. Cl.$^6$ ................................................. B32B 9/00
[52] U.S. Cl. .................. 428/195; 428/1; 428/913; 430/273.1; 430/330; 346/135.1
[58] Field of Search ................... 428/195, 457, 428/461, 463, 913, 1; 430/273, 330, 346, 945; 346/76.2, 135.1

[56] References Cited

U.S. PATENT DOCUMENTS

| | | | |
|---|---|---|---|
| 4,306,014 | 12/1981 | Kunikane | 430/338 |
| 4,415,650 | 11/1983 | Kido | 430/273 |

Primary Examiner—Patrick Ryan
Assistant Examiner—Patrick Jewik
Attorney, Agent, or Firm—Ernestine C. Bartlett

[57] ABSTRACT

Chemical substances are provided which exhibit thermally induced spin transitions between two stable spin states at ambient temperature, said transitions being associated with a hysteresis phenomenon and resulting in an abrupt variation of the color of the molecules for realizing a medium for storing, processing and/or displaying information by way of thermal writing, optical reading and thermal erasing, a particular embodiment of such a medium comprising at least a layer of chemical substances including a lattice with a molecule comprising a metallic element $Fe_{(II)}$, or $Fe_{(II)}$ or $Co_{(II)}$ associated with at least one ligand chosen from the substituted triazoles which are defined by the formula:

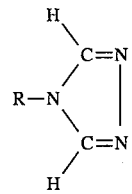

in which R is H or an alkyl $C_n H_{2n+1}$ or R is an amine group $NL_2$ where L is H and an alkyl radical, said molecule also comprising one or several anions chosen, for example, from $BF_4^-$, $ClO_4^-$, $Br^-$, $Cl^-$, and the lattice containing a defined quantity of non-ligand water, ensured by the presence of a hygroscopic substance.

19 Claims, 5 Drawing Sheets

SPIN-TRANSITION COMPOUNDS AND THEIR USE FOR STORING, PROCESSING AND/OR DISPLAYING INFORMATION

This is a continuation-in-part of application Ser. No. 979,104, filed Nov. 20, 1992, now abandoned.

FIELD OF THE INVENTION

The invention relates to spin-transition compounds and their use for storing, processing and/or displaying information.

BACKGROUND OF THE INVENTION

Spin-transition compounds and their use for storing information are already known from Patent Application EP 0 251 043. Generally, the compounds known for this use belong to the group of transition metals such as iron and cobalt and preferably $Fe_{II}$ or $Co_{II}$, associated with a ligand.

Said Patent Application gives the following examples:
a) [Fe(2-amino methyl pyridine)$_3$]Cl$_2$, EtOH
b) [Fe(1,10-phenantholine)$_2$(NCS)$_2$]
c) [Fe(1-propyl tetrazole)$_6$](BF$_4$)$_2$ For storing information these materials use the LIESST phenomenon (Light Induced Excited Spin-State Trapping). The LIESST phenomenon is a molecular process in which a spin transition is induced optically.

The use of the known materials in accordance with the LIESST phenomenon is based on the existence of two potential wells, one corresponding to a low spin state and the other corresponding to a high spin state, separated by a potential barrier.

At a temperature which is lower than a critical temperature Tc of the order of 50K, the low spin state is a stable state. This is known from a publication describing the general state of the technique in this field, entitled "Spin-Transition Molecular System; towards Information Storage and Signal Processing" by J. Zarembowitch and O. Kahn in NEW JOURNAL OF CHEMISTRY, Vol. 15, 1991, pp. 181–190. Page 183 of this publication states the Gibbs equation which is defined by:

$$\Delta G = G_{HS} - G_{LS} = \Delta H - T\Delta S$$

in which $\Delta G$ is the energy variation corresponding to the spin transition of a given quantity of material, $\Delta H$ is the enthalpy variation T is the temperature $\Delta S$ is the entropy variation.

At a low temperature the enthalpy is predominant and the low spin state is the more stable phase, i.e. the phase of lower Gibbs free energy.

The LIESST phenomenon is described on page 185, column 2 of the above-mentioned publication. First, the compound is illuminated in its stable low spin state with radiation having a given wavelength, for example, by means of a laser beam. This illumination induces unstable excited high spin states. These states decay rapidly via allowed transitions, as is shown in FIG. 9 on page 185 of the afore-mentioned publication. The electrons may follow two relaxation paths. In the first path they fall back directly into the first potential wells via allowed transitions, i.e. at the stable low spin ground state. In the other path they fall into the second potential wells corresponding to a high spin state which is not stable, but metastable. When the compound is at a very low temperature, thermal perturbation will have a minor effect. The electrons thus remain trapped in the high metastable spin state during a period of time which is sufficiently long to accumulate enough energy to exceed the potential barrier. Subsequently they fall back into the first potential wells corresponding to the stable low spin state. The period of time during which the system remains in the metastable state may be of the order of a quarter of an hour.

The compounds utilizing the LIESST phenomenon may have a memory effect which is suitable for storing information.

However, in connection with the LIESST phenomenon, the use of these compounds has several drawbacks:

they can only be used at very low temperatures, their memory effect is very volatile, they do not have two stable states but a single one, because they present no hysteresis in the range of temperatures considered.

Nevertheless, they are inscribable and optically readable, because the spin transition is accompanied by a structural change of the molecule, related to a varying metal-ligand bond length. This structural change of the spin state becomes manifest as an abrupt color change.

The known materials are thermally erasable, which is effected spontaneously.

The invention has for its object to provide a medium which is inscribable, readable, erasable and reinscribable at ambient temperature, and can be used for storing, processing and/or displaying information.

SUMMARY OF THE INVENTION

According to the invention, said problems are solved by a medium for storing, processing and/or displaying information comprising at least one layer of chemical substances exhibiting thermally induced spin transitions between two stable spin states at ambient temperature, said transitions being associated with a hysteresis phenomenon and resulting in a variation of the metal-ligand bond length and an abrupt variation of the color of the molecules.

In an advantageous embodiment the chemical substances include a lattice with a molecule formed from $Fe_{(II)}$, or $Fe_{(III)}$ or $Co_{(II)}$ associated with at least one ligand chosen from the substituted triazoles hereafter referred to in abbreviated form as a "Trz" or as "Trzs", the invention being directed to the use of Trzs which are defined by the formula:

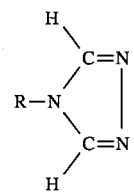

in which R is, for example, H or an alkyl $C_n H_{2n+1}$ or R is a $NL_2$ group where L is chosen between H and an alkyl, said molecule also comprising one or several anions chosen, for example, from $BF_4^-$, $ClO_4^-$, $CO_3^{2-}$, $Br^-$, $Cl^-$, and this lattice containing a defined quantity of non-ligand water, ensured by the presence of a hygroscopic substance.

BRIEF DESCRIPTION OF THE FIGURES

The invention will hereinafter be described in greater detail with reference to FIG. 1 which shows the enthalpy $\Delta H$ corresponding to the spin transition of a given quantity of material, for example, 1 mole, as a function of an internal coordinate, for example, the metal-ligand bond length, FIG. 2 which shows a hysteresis cycle associated with the spin transition of the selected materials, FIGS. 3a and 3b which illustrate the influence of water in the lattice of a complex as described herein; FIGS. 4a to 4f which illustrate the influence of doping the main ligand by a small quantity of a second ligand.

DETAILED DESCRIPTION OF PREFERRED EMBODIMENTS

Figure 1:
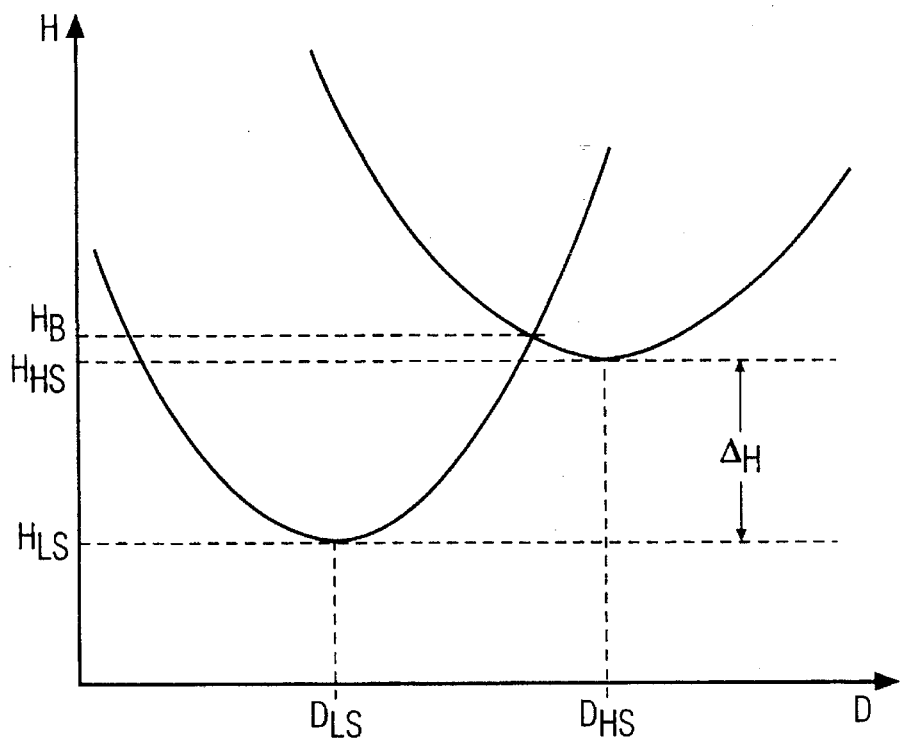

To solve the problem of storing, processing and/or displaying information according to the invention, a compound with a coordination complex of $Fe_{(II)}$, $Fe_{(III)}$ or of $Co_{(II)}$ may be used.

This complex is associated with a Trz ligand which is, for example a substituted triazole defined by the formula:

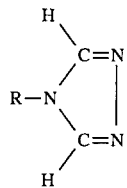

in which R is H, an alkyl $C_n H_{2n+1}$ or the amine $NL_2$ where L may be H or an alkyl. This complex also comprises one or several anions chosen for example from $BF_4^-$, $ClO_4^-$, $CO_3^{2-}$, $Br^-$, $Cl^-$.

Suitable compounds for use herein are coordination complexes of iron and cobalt with triazole ligands having the above formula that are capable of exhibiting thermally induced spin transitions between two stable spin states at ambient temperature, said transitions being associated with a hysteresis phenomenon and resulting in a variation of the metal-ligand bond length and a variation of the color of the molecules of said chemical substances.

Suitable complexes for use in the invention include:

I. Triazole ligand complexes of Fe(II) such as
 a) Fe (H Trz)$_3$ (BF$_4^-$)$_2$
 b) Fe (H Trz)$_3$ Cl$_2$
 c) Fe (H Trz)$_3$ (ClO$_4^-$)$_2$
 d) Fe (H Trz)$_3$ (CO$_3^{2-}$)
 e) Fe (H Trz)$_3$ Br$_2$ wherein H Trz is a ligand of the above formula wherein R is H;

II. Amino-triazole complexes of Fe (II) such as
 a) Fe (NH$_2$ Trz)$_3$ (BF$_4^-$)$_2$
 b) Fe (NH$_2$ Trz)$_3$ Cl$_2$
 c) Fe (NH$_2$ Trz)$_3$ (ClO$_4^-$)$_2$
 d) Fe (NH$_2$ Trz)$_3$ (CO$_3^{2-}$)
 e) Fe ( NH$_2$ Trz)$_3$ Br$_2$
 wherein NH$_2$Trz is a ligand of the above formula when R is an amino group;

III. Triazole triazolate ligand complexes of Fe (II) such as
 a) Fe (Trz) (Htrz)$_2$ (BF$_4^-$)
 b) Fe (H Trz)$_2$ (NL$_2$ Trz) Cl$_2$
 c) Fe (H Trz)$_2$ (NL$_2$ Trz) (ClO$_4^-$)$_2$
 d) Fe (H Trz)$_2$ (NL$_2$ Tr$_3$) (CO$_3^{2-}$)
 e) Fe (H Trz)$_2$ (NL$_2$ Trz) Br$_2$
 f) Fe (Trz$^-$) (H Trz) (NL$_2$ Trz) (BF$_4^-$)
 g) Fe (Trz$^-$) (H Trz) (NL$_2$ Trz) (Cl$^-$)
 h) Fe (Trz$^-$) (H Trz) (NL$_2$ Trz) (ClO$^{4-}$)
 i) Fe$_2$ (Trz$^-$) (H Trz)$_2$(NL$_2$ Trz)$_2$(CO$_3^{2-}$)
 j) Fe (Trz$^-$) (HTrz) (NL$_2$Trz) (Br$^-$)
 k) Fe (Trz$^-$) (NL$_2$ Trz)$_2$ (Cl$^-$)
 l) Fe (Trz$^-$) (NL$_2$Trz)$_2$ (ClO$_4^-$)
 m) Fe$_2$ (Trz$^-$)$_2$(NL$_2$Trz)$_4$ (CO$_3^{2-}$)
 n) Fe (Trz$^-$) (NL$_2$Trz)$_2$ (Br$^-$)
 o) Fe (RTrz) (NL$_2$Trz)$_2$ (BF$_4^-$)$_2$
 p) Fe (RTrz) (NL$_2$Trz)$_2$ CL$_2$
 q) Fe (RTrz) (NL$_2$Trz)$_2$ (ClO$_4^-$)$_2$
 r) Fe (RTrz) (NL$_2$Trz)$_2$ (CO$_3^{2-}$)
 s) Fe (RTrz) (NL$_2$Trz)$_2$ Br$_2$ IV. Triazole-aminotriazole ligands of Fe (II) such as
 a) Fe (Trz$^-$) (H Trz)$_2$ (BF$_4^-$)
 b) Fe (Trz$^-$) (HTrz)$_2$ (Cl$^-$)
 c) Fe (Trz$^-$) (HTrz)$_2$ (ClO$_4^-$)
 d) Fe$_2$ (Trz$^-$)$_2$ (HTrz)$_4$ (CO$_3^{2-}$)
 e) Fe (Trz$^-$) (HTrz)$_2$ (Br$^-$)
 f) Fe (RTrz)$_3$ (BF$_4^-$)$_2$
 g) Fe (RTrz)$_3$ Cl$_2$
 h) Fe (RTrz)$_3$ (ClO$_4^-$)$_2$
 i) Fe (RTrz)$_3$ (CO$_3^{2-}$)
 j) Fe (RTz)$_3$ Br$_2$
 k) Fe (Trz$^-$) (RTrz)$_2$ (BF$_4^-$)
 l) Fe (Trz$^-$) (RTrz)$_2$ (Cl$^-$)
 m) Fe (Trz$^-$) (RTrz)$_2$ (ClO$_4^-$)
 n) Fe$_2$ (Trz$^-$)$_2$ (RTrz)$_4$ (CO$_3^{2-}$)
 o) Fe (Trz$^-$) (RTrz)$_2$ (Br$^-$)
 p) Fe (HTrz) (NL$_2$ Trz)$_2$ (BF$_4^-$)$_2$
 q) Fe (HTrz) (NL$_2$ Trz)$_2$ Cl$_2$
 r) Fe (HTrz) (NL$_2$ Trz)$_2$ (ClO$_4^-$)$_2$
 s) Fe (HTrz) (NL$_2$ Trz)$_2$ (CO$_3^{2-}$)
 t) Fe (Htrz) (NL$_2$ Trz)$_2$ Br$_2$
 u) Fe (RTrz)$_2$ (NL$_2$ Trz) (BF$_4$)$_2$
 v) Fe (RTz)$_2$ (NL$_2$ Trz) Cl$_2$
 w) Fe (RTrz)$_2$ (NL$_2$ Trz) (ClO$_4^-$)$_2$
 x) Fe (RTrz)$_2$ (NL$_2$ Trz) (CO$_3^{2-}$)
 y) Fe (RTrz)$_2$ (NL$_2$ Trz) Br$_2$
 z) Fe (Trz$^-$) (RTrz) (NL$_2$ Trz) (BF$_4^-$)
 aa) Fe (Trz$^-$) (RTrz) (NL$_2$ Trz) (Cl$^-$)
 bb) Fe (Trz$^-$) (RTrz) (NL$_2$ Trz) (ClO$_4^-$)
 cc) Fe (Trz$^-$) (RTrz) (NL$_2$ Trz) (CO$_3^{2-}$)
 dd) Fe (Trz$^-$) (RTrz) (NL$_2$ Trz) (Br$^-$)

All of the above complexes have been obtained by combining Fe(II) with the above-mentioned ligands and the above-mentioned anions. A great number of other complexes may be obtained in the same way.

The lattice may contain a defined quantity of non-ligand water, i.e. the water does not have a direct bond with the metal and is thus not present in the molecule. Nevertheless, this quantity of water influences the triazole ligands because it has its effect on the bonding strength. It is indispensable. Thus, to retain it, the lattice contains a hygroscopic chemical substance.

The complex compounds may be produced by methods well known in the art. For example, Fe (BF$_4$)$_2$, which is a precursor of the material, may be chosen as a hygroscopic molecule. A valid method of preparation is to combine the ligand and an iron salt such as Fe $(BF_4)_2$ in an acid solution and to cause them to react, which results in a precipitate, and to subsequently recover the useful product in the form of a powder.

A defined quantity of water is captured by using an excess of Fe $(BF_4)_2$ in this method of preparation.

Suitable methods for preparing suitable complexes for use in the invention are disclosed in L. Naturforsch: 85a pp. 852–864 (1980) by D. W. Engelfriet and W. L. Groeneveld and/or in Z. Naturforsch, 32b, 533–536 (1977) by J. G. Haasnoot and W. L. Groeneveld, which methods are incorporated herein by reference.

FORMATION OF MEDIA FOR STORING, PROCESSING OR DISPLAYING INFORMATION

The materials selected in accordance with the invention are compounds exhibiting thermally induced spin transitions. These spin transitions are accompanied by structural and electronic modifications of the molecules. These modifications bring about an abrupt change of the absorption spectrum of the molecules and thus of the color of the compounds, the transitions between the electronic levels having become different.

In the low spin (LS) state the compounds are dark purple, whereas in the high spin (HS) state these compounds are chalk white. Thus, there is a great contrast between the colors of the compounds in each spin state (LS or HS).

This macroscopic phenomenon is thus easily perceptible, because the dynamic range of the optical signal related to the abrupt color variation is very large during a spin transition.

The advantage is that the variations of this optical signal can be detected by a low-sensitivity detection system, i.e. a system which is inexpensive and is easy to implement.

In relation to these spin transitions the selected compounds have numerous other advantageous properties.

Each spin state (LS or HS) is a preferably stable state at ambient temperature. Samples formed in the one or the other state are maintained at ambient temperature for months without showing any sign of change. The two states (LS and HS) are stable in a concomitant manner.

An elaborate study of these materials has proved that they have a delay effect during spin transitions, which effect is due to the molecular cooperativity resulting in a hysteresis phenomenon which, in accordance with the material chosen, may range between several degrees of Celsius to several dozen degrees of Celsius, i.e. between −20° and 100° C., which is a temperature range suitable for industrial applications.

When a thermal perturbation is applied, the cooperativity results in:

(a) either all the molecules undergoing a spin transition simultaneously, or (b) none of the molecules undergoing a spin transition.

These properties are thus completely different from those of the materials known in the prior art.

In these known materials, the spin transitions are optically induced from LS to HS and thermally induced from HS to LS; they are not associated with a hysteresis phenomenon. There is only a stable state (LS) and a metastable state (HS) which are only concomitant at a very low temperature.

The materials selected in accordance with the invention present thermally induced spin transitions, both the transition from LS to HS and for the transition from HS to LS; these transitions are associated with a hysteresis phenomenon; the two states HS and LS are perfectly stable in a concomitant manner at ambient temperature.

STORING, PROCESSING OR DISPLAY DEVICES

The compounds selected in accordance with the invention may also be used as memory materials which are thermally inscribable and erasable and optically readable and can thus be used for storing, processing or displaying information.

For example, an infrared laser beam or a visible laser such as Ar or He Ne may be used for thermal addressing. The pixel resolution is the same as that of the laser beam used. An electronic beam having a definition of $\leq 100$ nm may alternatively be used.

The information may be fully erased by cooling below the transition temperature of the low spin state. The information may alternatively be erased partially. Localized Peltier elements may advantageously be used for this purpose.

Optical reading may be effected in transmission or in reflection. This choice depends only on the support used for the selected spin transition material. For example, one CCD or diode strip (or strips) may be used for optical reading. Reading is realized in the visible range with the materials described in the examples below.

The materials described in the examples may therefore also be used for directly displaying information on a display screen. The screen should have a dark background matching with the dark purple color, for example, of the materials in the low spin state (LS). The display will then show in a very clear white on this dark background.

The product can form surfaces which are much larger than the liquid crystals. This is one of the extremely important advantages over liquid crystals. For example, deposition of powders is the only method to be used, whereas the liquid crystals necessitate the use of a capacitor, viz. a transistor per pixel.

Another advantage of products according to the invention is their stability: once stabilized in the hysteresis zone, the material can indefinitely retain its addressing without supply of energy and without refreshing the signal.

The selected compounds may thus be used in products as substitutes for liquid crystals, with the very considerable advantage that, dependent on the support used, the product obtained for forming a screen will be much less fragile than the liquid crystal products and will also show a much greater contrast.

DISPLAY SCREENS AND PLATES

The selected compound, which has previously been pulverized, may be deposited as a layer on a support by means of various methods.

The compound may particularly be deposited on a solid support by means of pulverization or by silk screen printing, or it may be incorporated in a synthetic material and deposited on such a support by means of a "whirl" method. It may even be deposited in the form of a powder and adhered to a synthetic material whose adhesive properties change after irradiation, a technique referred to as the "phototacky" method.

The support may be made of glass, a polymer of the type of PMMA (polymethyl methacrylate), polycarbonate, or PVC, or a ceramic material.

The selected compound may also be incorporated directly in a matrix, for example of the polymer type.

ADDITIONAL PROPERTIES OF COMPLEXES OF THE INVENTION

As a function of an internal coordinate such as, for example, the metal-ligand bond length D, FIG. 1 shows the enthalpy variation ΔH related to the Gibbs equation:

$$\Delta G = G_{HS} - G_{LS} = \Delta H - T\Delta S,$$

in which ΔH is the enthalpy variation,

T is the temperature,

ΔS is the entropy variation, and

ΔG is the difference of the Gibbs free energies related to the HS and LS states.

The spin transition of the materials according to the invention is based on the existence of two potential wells, one corresponding to the low spin state LS (see FIG. 1) and the other corresponding to the high spin state HS. These potential wells are separated by a potential barrier. The bottoms of the potential wells correspond to the energy levels $H_{LS}$ and $H_{HS}$. The energy relating to the potential barrier is denoted by $H_B$.

The energy difference between the bottoms of the two potential wells is the variation ΔH related to the Gibbs free energy given above.

By applying a thermal perturbation to one of the selected compounds, which is first in the low spin stable state (LS), in which state the electrons are trapped in the first potential wells, unstable excited high spin states are induced, whereafter the electrons fall back via allowed transitions by following a principal relaxation path which is the path of the second potential wells corresponding to a perfectly stable high spin state in the ambient temperature range. The electrons remain trapped in the second potential wells corresponding to HS and because of the hysteresis phenomenon they do not spontaneously return to the first potential wells corresponding to LS. For regaining this LS state it is necessary to cool the compound beyond the hysteresis domain instead of heating it, as is known in the prior art.

Figure 2:
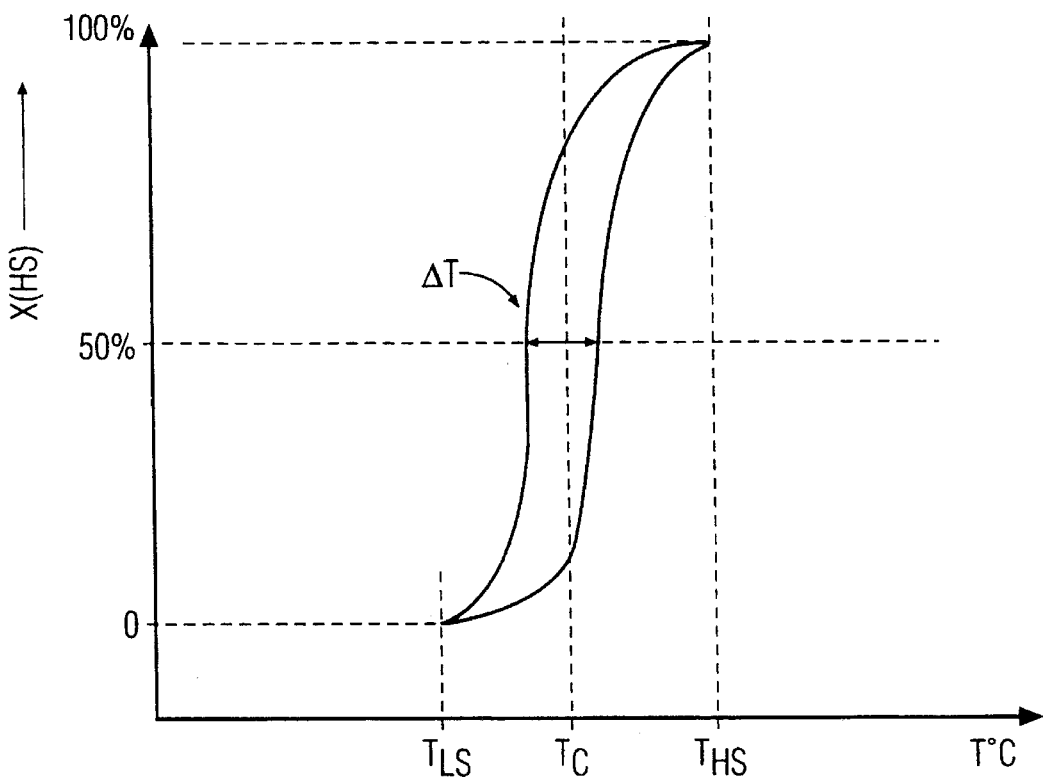

FIG. 2 shows such a hysteresis cycle. The molar fraction X of the material undergoing spin transition at a temperature of T is plotted on the ordinate and the temperature T is plotted on the abscissa and X is the molar fraction of high spin (HS) material.

The stability of each LS and HS phase is determined by this difference ΔG in the Gibbs free energy corresponding to the spin conversion of a given quantity of material, for example 1 mole. It is thus very important to take the relative values of the terms ΔH and TΔS into account.

As stated hereinbefore, the thermodynamical conditions have been chosen in such a way that the selected compounds taken as examples have two stable states at ambient temperature. At this temperature, in contrast to what is known in the prior art, the entropy term TΔS in the Gibbs equation may become non-negligible in certain thermodynamical conditions. With reference to the Gibbs equation and FIG. 1 it should therefore be noted that according to whether the term ΔG is larger and more negative, the phenomena related to a spin transition are more likely to occur.

The entropy term TΔS thus plays an important role in the phenomenon utilized for carrying the invention into effect. It involves the use of a spin degeneracy term and a lattice term.

The spin degeneracy term relates to the degeneracy of atomic states. The degeneracy term is given by formula:

$$2s+1$$

in which s is the value of the spin. The degeneracy term varies between 1 and 5.

The entropy variation ΔS is thus larger as the spin state s is larger. In fact, the term ΔS is given by the relation $$\Delta S = R l_n \frac{(2s+1)\,(HS)}{(2s+1)\,(LS)}$$

in which R is the ideal gas constant.

In the case where the compound is a complex of $Fe_{II}$, s=0 for the LS state and s=2 for the HS state.

In the case where the compound is a complex of $Fe_{III}$, s=½ for the LS state and s=5/2 for the HS state.

In the case where the compound is a complex of $Co_{II}$, s=½ for the LS state and s=3/2 for the HS state.

The result is that the complexes of $Fe_{II}$ are particularly interesting.

On the other hand, the lattice term results in its turn from the use of a thermal disorder term, which is a function of the temperature T, and of an order or structural term.

For example, a compound having bridges between metallic nuclei implies the existence of a short distance order factor.

All these factors play an important role in the existence of spin transitions in a given temperature range, and the desired results can be obtained by making a compromise between their values, which results are:

an optical contrast between the correct low spin state and the correct high spin state, improvement of the stability in each high spin state and low spin state, a critical temperature Tc at ambient temperature, a sufficient width ΔT of the hysteresis cycle (see FIG. 2).

Knowledge of these parameters thus enables those skilled in the art to make a choice of the spin transition compound which is best adapted to the envisaged application.

If the entropy ΔS decreases, the LS state is stabilized at increasingly higher temperatures T. Consequently, the critical temperature Tc is increased (see FIG. 2).

On the other hand, as the cooperativity in a complex is greater, the delay effect is larger and the hysteresis phenomenon, i.e. ΔT in FIG. 2, is more important.

Moreover, as the difference between the spin states is greater, the magnetic effect related to the spin transition is better detectable. The more the entropy term ΔS is increased, the lower the transition temperature (note: the term to be considered T×ΔS).

On the other hand, as the degeneracy is lower, the magnetic effect related to the spin transition is less detectable, because there is a small difference in magnetic states.

A compromise should thus be found between a degeneracy term which is high enough to involve a perceptible spin effect and not too high to remain within an ambient temperature range which is suitable for industrial applications.

By inducing the order in the structure by creating bridges between metallic nuclei, ensured by a ligand which is common to the two metallic ions (short distance order), the entropy term ΔS is reduced and the thermal state has less influence on the spin transitions, while the stability of the LS state at higher temperatures is enhanced.

For establishing the spin transition phenomenon in the ambient temperature range the compounds selected according to the invention will have:

at least one triazole ligand,
preferably between 3 and 6 ligands,
preferably a mixture of ligands.

TABLE I

| compound ligand | Prior art tetrazole | Product no. 1 Amino triazole $NH_2$-Trz | 2 Amino triazole $NH_2$-Trz | 3 Triazole triazolate H-Trz, Trz$^-$ | 4 Triazole H-Trz, H-Trz |
|---|---|---|---|---|---|
| N | 6 | 3 to 5 | 3 to 5 | 3 to 5 | 3 to 5 |
| R | propyl | $NH_2$ | $NH_2$ | H | H |
| A | $BF_4^-$ | $BF_4^-$ | $BR^-$ | $BF_4^-$ | $BF_4^-$ |
| Tc | $-160°$ C. | $-20°$ C. | $+30°$ C. | $+70°$ C. | $+40°$ C. |
| $\Delta$T |  | $\approx 10°$ C. | $\approx 15°$ C. | $\approx 40°$ C. | $\approx 30°$ C. |

In the Table, the prior art product is a complex having the generalized formula Fe (II) (Propyl Trz)$_3$ $(BF_4^-)_2$ as described in EPO 251 043; Product No. 1 has the generalized formula Fe (II) $(NH_2Trz)_3(BF_4^-)_2$, $6H_2O$; Product No. 2 has the generalized formula Fe(II) $(NH_2Trz)_3$ Br$_2$; Product No. 3 has the generalized formula Fe (II) (Trz$^-$) (HTrz)$_2$ $(BF_4^-)$, $6H_2O$; and _ Product No. 4 has the generalized formula Fe(II) (HTrz)$_3$ $(BF_4^-)_2$ $6H_2O$.

Table I above gives examples of critical temperatures Tc of the hysteresis cycle and of the hysteresis width $\Delta$T to be expected as a function of the different ligands.

The compounds mentioned in this Table have less than 6 ligands. The products tested are numbered 1 to 4.

The results stated in Table I may be compared with those obtained from compounds known in the art including a propyl tetrazole. The temperature Tc is then $-160°$ C. (110K).

According to the invention, a mixture of materials is realized for adjusting the average temperature of the hysteresis phenomenon. Particularly, a high-temperature material is preferably used as a basic material, for example with reference to Table I, product no. 3 whose average temperature of the hysteresis phenomenon, or critical temperature, is Tc=$70°$ C. And in this case, at the moment of synthesis of the ligand, here triazole-triazolate, a very small quantity is added, for example, to obtain a concentration wherein X=0.1, approximately 5 mol % of the doping ligand, in this case an amino-triazole usually associated with a product, for example product no. 1, at a low temperature, which usually corresponds to a critical temperature Tc=$-20°$ C., and this mixture of the majority ligand, here triazole-triazolate, and the other ligand, here an amino-triazole, is made in a very small quantity as defined above. The favorable effect of the invention occurs however, whenever the doping ligand is present, even in amounts less than about 1 mol %. FIGS. 4a to 4d illustrate the effect of various quantities of doping ligand.

The method of preparation is continued by combining the material with the iron salt, as stated hereinbefore, thus obtaining a precipitate from which a powder is extracted.

This method of preparation, including two different ligands in the recommended quantities, yields a material for which the average temperature of the hysteresis phenomenon is $25 \leq Tc \leq 35°$ C. and the hysteresis $5° C. \leq \Delta T \leq 15°$ C.

For adjusting the average temperature Tc of the hysteresis phenomenon, a controlled disorder is introduced in a general manner into a material having a temperature Tc which is higher than the desired temperature Tc. This is effected by adding a very small quantity of the paramagnetic element to a product having a magnetic effect.

When the amino-triazole tends towards a low temperature, its molecular spin produces small magnetic dipoles which "encourage" the high-temperature material to tend towards a low temperature as well.

Table II shows the characteristics of the product No. 5 having the afore-described mixture of ligands. In the Table, the complex has the general formula
Fe(II)[HTrz)$_2$(Trz$^{-1}$)]$_{1-n}$($NH_2$Trz)$_n$ $BF_4^-$), $yH_2O$ where n and y are concentrations in the final product.

TABLE II

| Product No. 5 Ligand H-Trz-Trz $\geq$ 99% $NH_2$-Trz $\leq$ 1% | |
|---|---|
| Product N° 5 | Fe(II) [(HTrz)$_2$(Trz$^-$)]$_{1-0.1}$[$NH_2$ Trz]$_{0.1}$ $(BF_4^-)$ |
| Ligands | N° 1 [(HTrz)$_2$ (Trz$^-$)]$_{1-0.1}$ Triazole-Triazolate<br>N° 2 [$NH_2$ Trz]$_{0.1}$ Aminotriazole for doping |
| Anion | $(BF_4^-)$ |
| T$_c$ | 20 to $25°$ C. |
| $\Delta$T | 10 to $20°$ C. |

H-Trz is understood to be a triazole with R=H; $NH_2$-Trz is understood to be amino-triazole; and Trz$^-$ is understood to be a triazolate.

The mixture recommended in this case for obtaining product No. 5 is thus based on product No. 3 of Table I, with the triazole-triazolate ligand for which first a mixture of ligands on all the molecules has been realized. This means that there are 2 triazoles (H-Trz) and 1 triazolate (Trz$^-$) for each Fe ion. This material is perfectly defined and has a homogeneous formula. One must add 5 mol % of the doping ligand $NH_2$ Trz$_3$ to obtain a concentration n=0.1.

The recommended mixture of this product No. 3 of Table I, including a triazole-triazolate ligand, and an amino-triazole ligand corresponding to product No. 1 results in this product No. 5, i.e. with a triazole-triazolate-amino-triazole ligand in which the majority of the molecules is of the triazole-triazolate type and in which several Fe ligand bonds are found
either with 3 amino-triazoles
or with 1 or 2 amino-triazoles and the rest of the ligands being triazole.

An additional technical problem has been found during use, viz. the products in their white form may become yellow in the long run. This is due to the fact that there may be an excess of iron such as the presence of Fe $(BF_4)_2$ in the useful product. The non-ligand iron Fe$^{2+}$ has the tendency to oxidize in the presence of water in Fe$^{3+}$.

The white color is stabilized if such an excess of iron is avoided in the final product. This is achieved by introducing, during the method of preparation, a hygroscopic soluble colorless salt which is non-basic or weakly basic, for example, of magnesium or potassium perchlorate [K Cl O$_4$ or Mg (Cl O$_4$)$_2$] or of sodium perchlorate [Na Cl O$_4$].

In this method including the use of perchlorates all the properties of the product are maintained and there is no detrimental influence by the excess of iron. The product thus indefinitely keeps its perfectly white color, even in the presence of water.

Figure 3A:
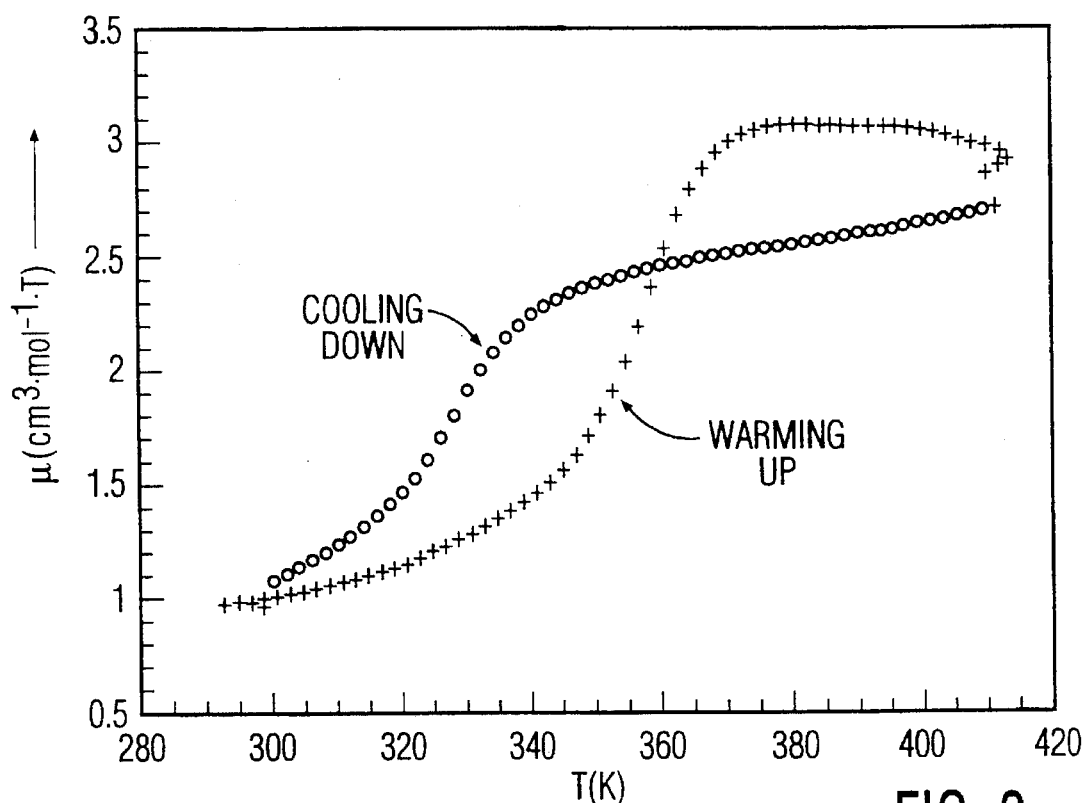
Figure 3B:
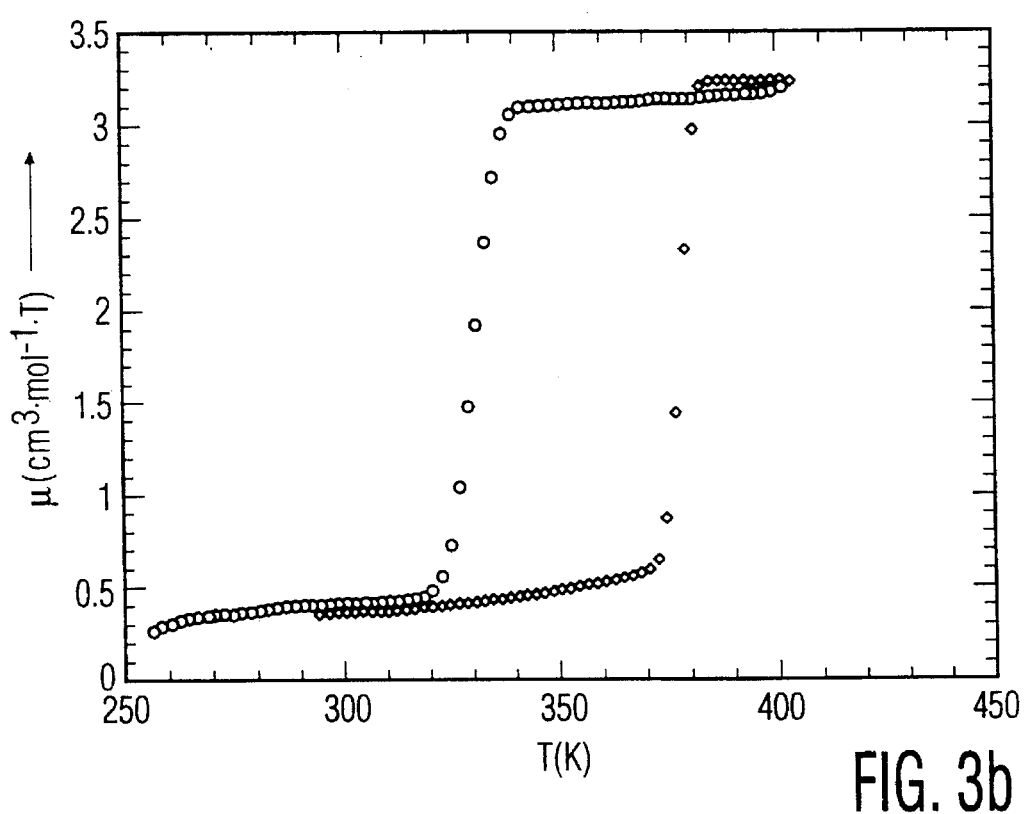

FIG. 3a and 3b illustrate the influence of water in the lattice of the product according to the invention.

These represent curves of $\mu$ versus T° (K)—where $\mu$ is the effective magnetic moment of the compound in cm$^3$. mol$^{-1}$. T, so $\mu$ is a direct function of X in FIG. 2. The curves of FIG. 3 show the hystersis of the compounds in the case of
Fe(II)(Trz$^-$)(HTrz)$_2$(BF$_4^-$) without water (FIG. 3a) and
Fe(II)(Trz$^-$)(HTrz)$_2$(BF$_4^-$), $6H_2O$ (FIG. 3b).

The hysteresis curve is centered on 350° K. It shows no ΔT when the lattice includes no water (FIG. 3a) and it shows ΔT≈40° when the lattice includes water (FIG. 3b).

FIG. 4a to 4d illustrate the influence of doping in the ligands of a product No. 6 according to the invention.

The considered product No. is now slightly different from product No. 5 of Table II. (only the anion is different).

Product No. 5 is $Fe(II)[(HTrz)_2(Trz^-)]_{1-n}$ $[NH_2Trz]_n$ $(BF_4^-)$, $6H_2O$.

Product No. 6 is $FE(II)[(HTrz)_2(Trz^-)]_{1-n}$ $[NH_2Trz]_n$ $(ClO_4^-)$, $6H_2O$.

Both products have $6H_2O$.

Figure 4A:
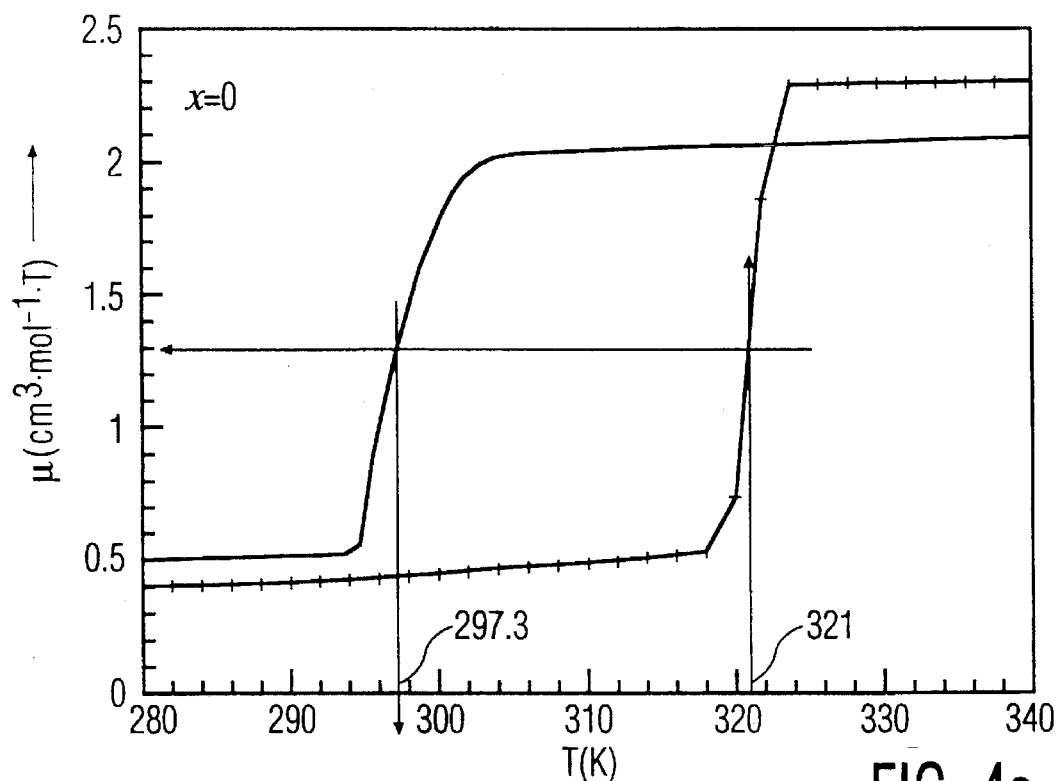
Figure 4B:
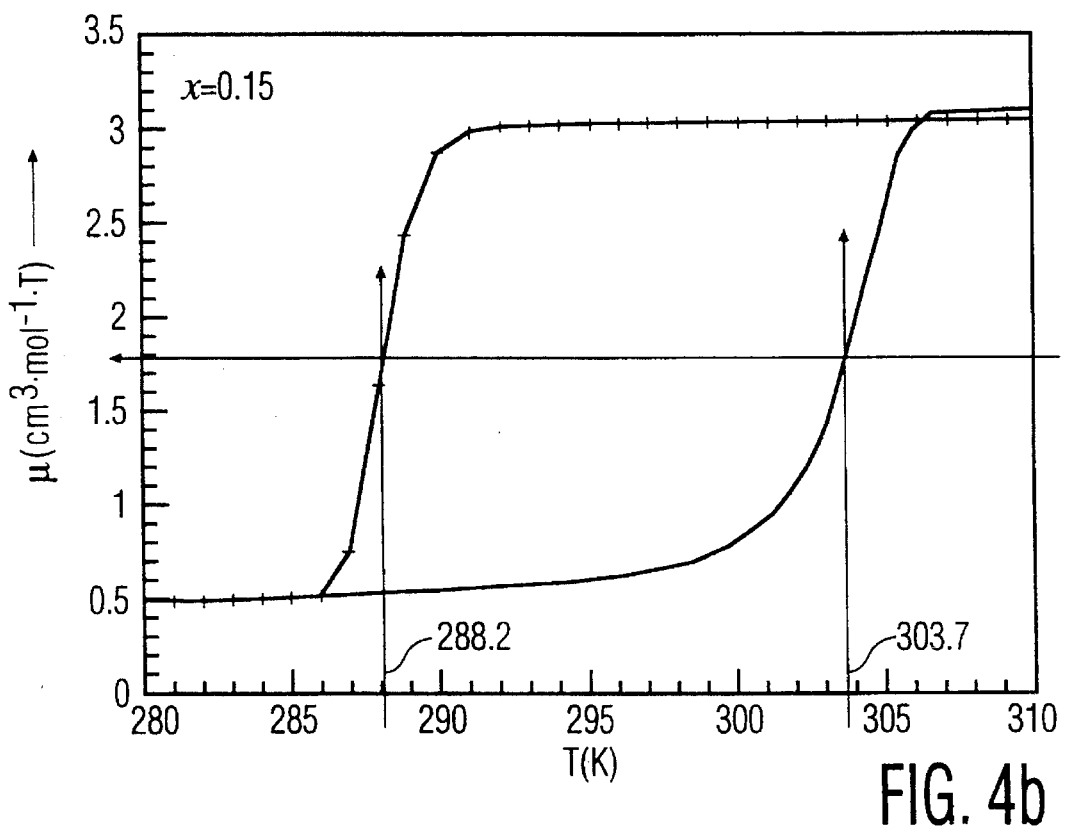

In FIG. 4a, n=0, which corresponds to no doping. In Product No. 6a $Fe(II)[HTrz)_2 (Trz^-)] (ClO_4^-)$, $6H_2O$. The hysteresis is centered on 310° K, ΔT=26°. In FIG. 4b, n=0.15 which corresponds actually to a slight doping. The hysteresis is shifted towards lower temperatures and exactly centered on 295.9° K (that means 22.9° C. which is room temperature).

Figure 4C:
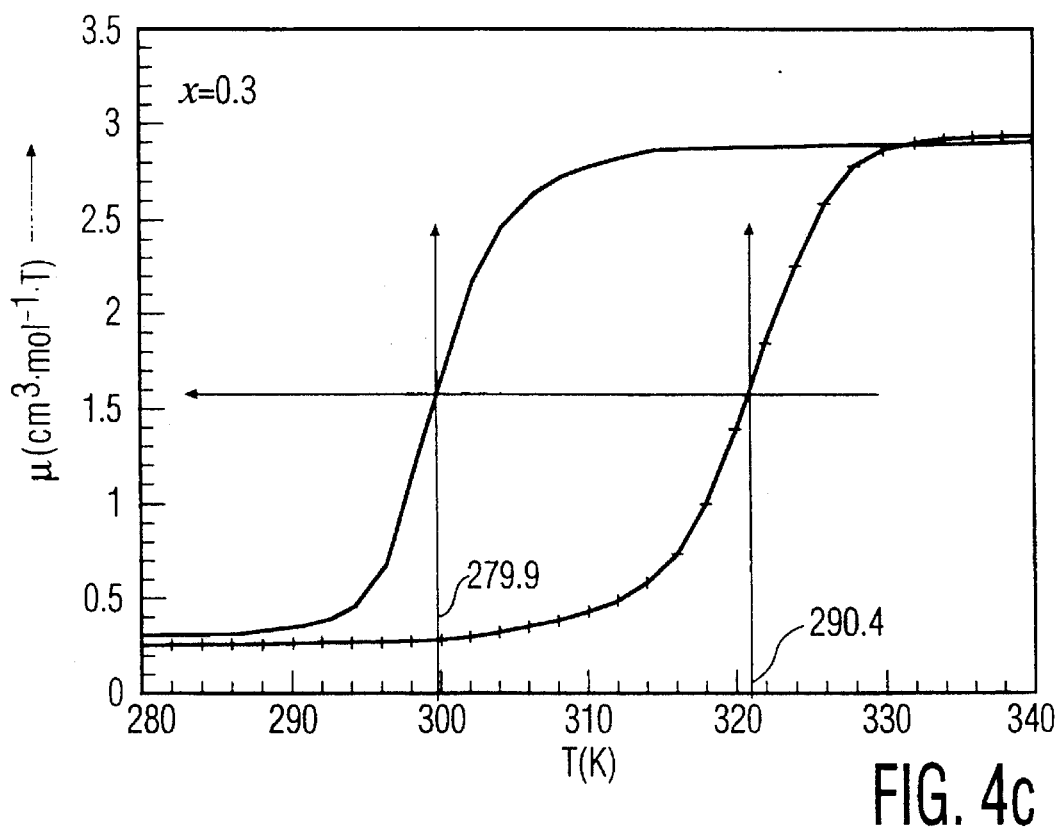

Product No. 6b
$Fe(II)[(HTrz)_2(Trz^-)]_{1-0.15}$ $[NH_2Trz]_{0.15}$ $(ClO_4^-)$, $6H_2O$
5 mol % of doping ligand must be added to obtain n=0.15
In FIG. 4c, n=0.3.

Figure 4D:
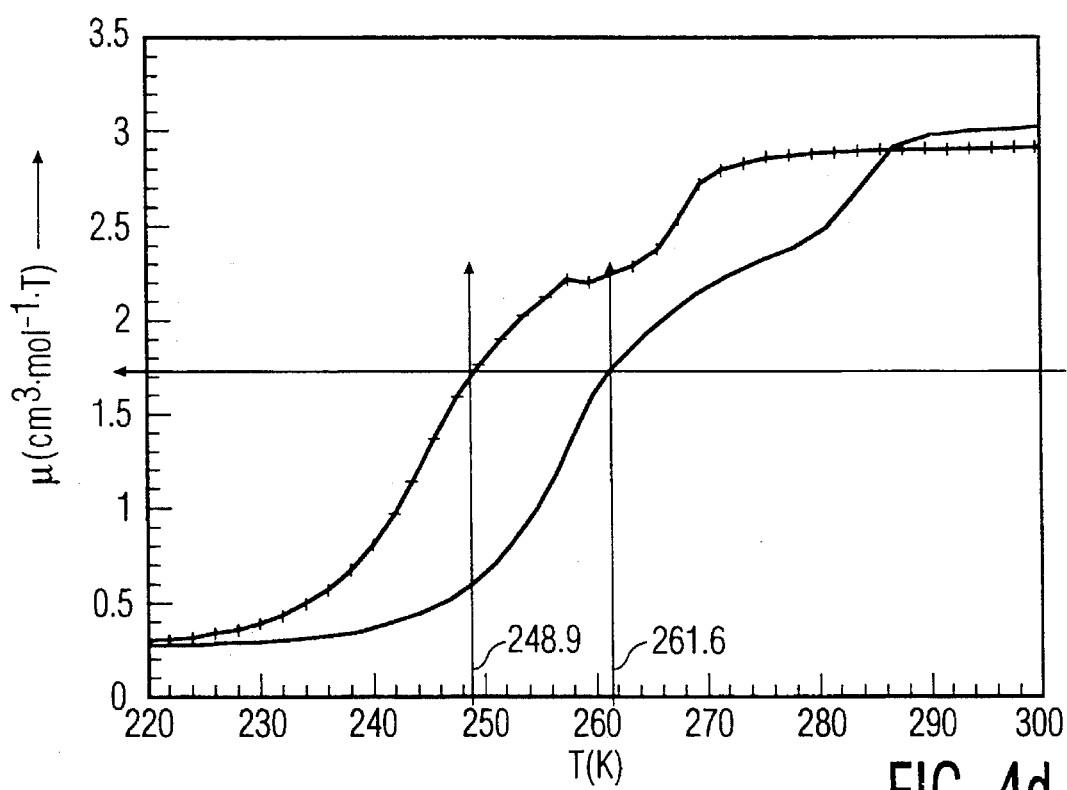

Product No. 6c
$Fe(II)[(HTrz)_2(Trz^-)]_{1-0.3}$ $[NH_2-Trz]_{0.3}(ClO_4^-)$, $6H_2O$
The hysteresis is now centered on 285.15° K, i.e. 12.15° C. It is too low with respect to room temperature (≈20° to 25° C.). ΔT≈21°. 10 mol. % of doping ligand must be added to obtain n=0.3. In FIG. 4d, n=0.6.

Product No. 6d
$Fe(II)[HTrz)_2(Trz^-)]_{1-0.6}[NH_2Trz]_{0.6}$ $(ClO_4^-)$, $6H_2O$ The hysteresis is now centered on 255° K, under the freezing point for water (273° K=0° C.). The sides of the hysteresis curve are no more steep. 20 mol % of doping ligand must be added to obtain n=0.6.

Figure 5:
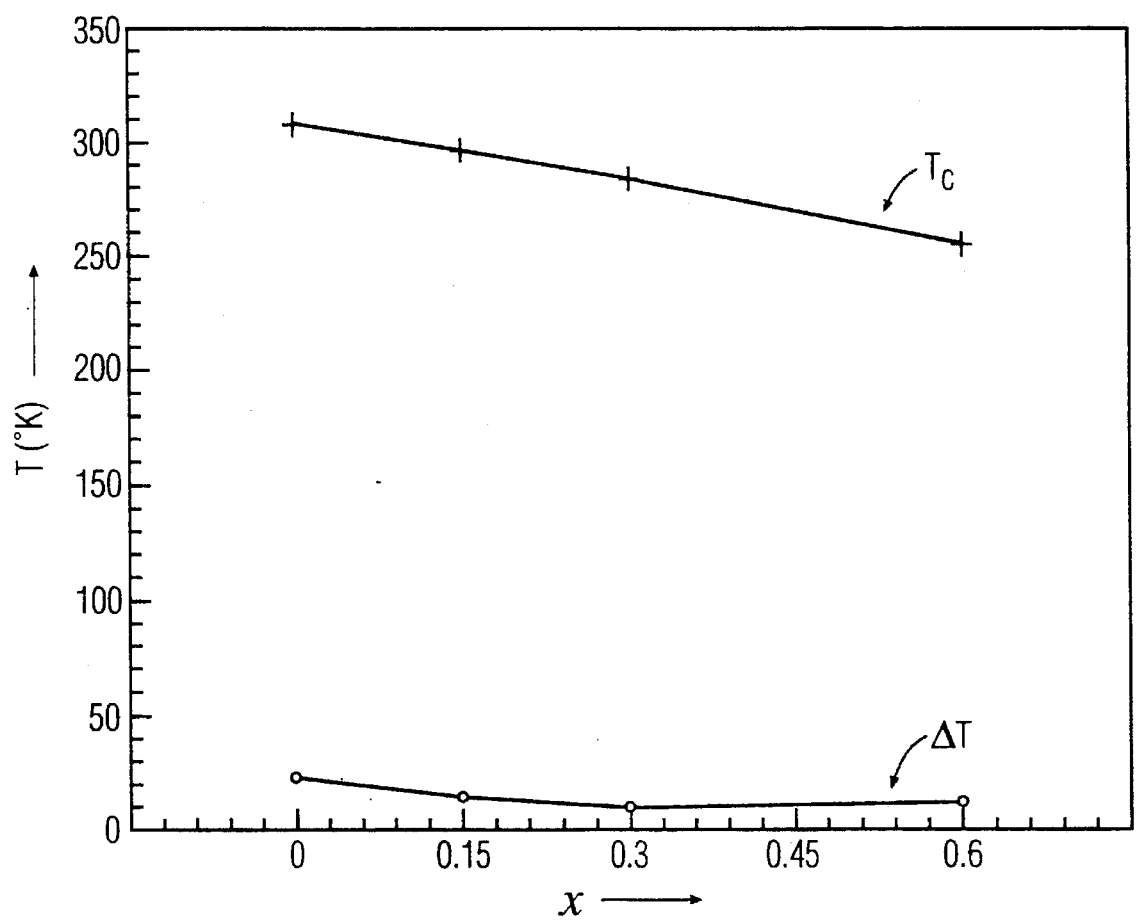
FIG. 5 which contains curves of Tc and ΔT of a doped product versus the concentration x of doping ligand of a given complex.

FIG. 5 shows $T_c$, the central points of hysteresis of the previous curves (FIG. 4a to FIG. 4d), and ΔT, versus n% of doping ligand.

It is taught by these curves that the result is best when n is not too high, that means in the case of this product, around 0.15.

The results are very sensitive to the doping, that is to say, the proportion of the second ligand added in small quantity in the complex, besides the first principal ligand.

DISPLAY SYSTEMS

A method of realizing a display system by means of the media comprising the compounds selected in accordance with the invention will hereinafter be described by way of example.

a) Active part—the medium including the (spin transition) compounds.

First, the method of realizing a display device comprises the realization of the medium constituted by the selected spin transition material which is deposited on a support in accordance with a method as described hereinbefore. The medium thus realized may be a plate having arbitrary dimensions, for example, very large or very small dimensions and any peripheral shape, for example, a square, rectangular, polygonal, circular or oval shape. The support may be rigid or flexible. Moreover, a large number of inexpensive non-brittle materials is very well suitable as a support for the spin transition compounds.

b) The thermal addressing device.
This device may be of the following types:
a heat pencil, for example, an infrared laser beam or a 520 mm laser, or a resistive heat pencil,
a matrix of x, y addressed resistive heat contacts. For this purpose, two crossed electrode lattices may be provided. In a particular embodiment the active medium may be disposed between the two electrode lattices with a system for dissipating the heat. For this purpose, the active medium may preferably be deposited as a thin film, for example by conventional vapor deposition in vacuo. In a modification it may be realized by vapor deposition of a solvent containing the powder of the active material. In a further modification the active material may be coated in a transparent polymerized matrix and associated with a localized thermal dissipation system for increasing the localized temperature. In a preferred embodiment the electrodes may be transparent and realized, for example, in InSnO (indium tin oxide).

The device may thus operate either in transmission or in reflection.

If the electrodes need not be transparent, they may be made of any conventional metal used for this purpose.

The advantage of the device including a matrix of electrodes x, y is that it can receive and display x, y coded messages, data or information.

According to the invention, the active medium may be used to realize a transmitter-receiver system, combined with a display or visualization of the transmitted message.

c) Erasing.
Erasing may be total by cooling or, in a modification, partial by using Peltier elements.

A display device realized by means of a storage medium according to the invention may advantageously be used to realize a display screen at very low cost for a memory card. As stated hereinbefore, the storage medium may include a synthetic support and is particularly adapted to cooperate with another synthetic support. Moreover, the storage medium may be extremely thin. Its use for realizing a screen which is able to display data stored on a memory card is thus particularly preferred.

Such a display device may also be used in numerous other devices in which the use of a fragile liquid crystal screen is undesired, particularly for displaying data relating to the operation of electric domestic appliances. The display device may also be used for calculators, audio and video apparatuses, game computers etc. and notably for monitor screens, and screens for urban or airport public address systems. Such a display device may replace a large number of liquid crystal applications but is not limited to these applications because it can be realized on very large supports.

This display device may be used, for example, as a "magic slate". A heat pencil is used in combination with a material of the type referenced material No. 3 in Table I, having a temperature Tc=70 and the hysteresis ΔT=40° C. This material is $Fe (HTrz)_2 (Trz^-)(BF_4)_1$. This material has an erasure time of approximately 30 seconds because of its high temperature Tc. Such a magic slate may be used for visualizing the data entered on a record carrier by means of a conventional touch-control panel.

What is claimed is:
1. A medium for storing, processing and/or displaying information comprising at least one layer of a chemical substance which exhibits a hysteresis phenomenon, wherein the chemical substance comprises:

(1) a metal-ligand complex having a first at least one ligand of substituted triazoles which are defined by the formula:

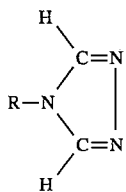

in which R is selected from the group consisting of an alkyl group and $NL_2$, wherein L is H or an alkyl group, said metal-ligand complex also comprising at least one anion selected from the group consisting of $BF_4^-$, $ClO_4^-$, $CO_3^{2-}$, $Br^-$, and $Cl^-$, (2) non-ligand water and (3) a hygroscopic substance, said hygroscopic substance ensuring the presence of non-ligand water, said medium being addressable, eraseable and re-addressable with data.

2. A medium as claimed in claim 1 wherein the metal-ligand complex comprises a metallic element $Fe_{(II)}$, or $Fe_{(III)}$ or $Co_{(II)}$.

3. A medium for storing, processing and/or displaying information comprising a chemical substance which exhibits a hysteresis phenomenon, wherein the chemical substance comprises:

(1) a metal-ligand complex having a first at least one ligand of substituted triazoles which are defined by the formula:

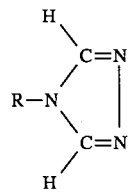

in which R is selected from the group consisting of an alkyl group and $NL_2$, wherein L is H or an alkyl group, said metal-ligand complex also comprising at least one anion selected from the group consisting of $BF_4^-$, $ClO_4^-$, $CO_3^{2-}$, $Br^-$, and $Cl^-$, (2) non-ligand water and (3) a hygroscopic substance, said hygroscopic substance ensuring the presence of non-ligand water, said medium being inscribable, eraseable and re-inscribable with data at ambient temperature.

4. A medium for storing, processing and/or displaying information comprising a chemical substance which exhibits a hysteresis phenomenon, wherein the chemical substance comprises:

(1) a metal-ligand complex having a first at least one ligand of substituted triazoles which are defined by the formula:

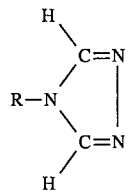

in which R is selected from the group consisting of an alkyl group and $NL_2$, wherein L is H or an alkyl group, said metal-ligand complex also comprising at least one anion selected from the group consisting of $BF_4^-$, $ClO_4^-$, $CO_3^{2-}$, $Br^-$, and $Cl^-$; and (2) non-ligand water, said medium being addressable, eraseable and re-addressable with data.

5. A medium for storing, processing and/or displaying information as claimed in claim 4, wherein the metal-ligand complex is selected from the group consisting of triazole ligand complexes of Fe(II) having the formulae a) $Fe\ (H\ Trz)_3\ (BF_4^-)_2$
b) $Fe\ (H\ Trz)_3\ Cl_2$
c) $Fe\ (H\ Trz)_3\ (ClO_4^-)_2$
d) $Fe\ (H\ Trz)_3\ (CO_3^{2-})$ and
e) $Fe\ (H\ Trz)_3\ Br_2$ wherein Htrz is a triazole ligand of the formula when R is H.

6. A medium for storing, processing and/or displaying information as claimed in claim 4, wherein the metal-ligand complex is selected from the group consisting of triazole ligand complexes of Fe(II) having the formulae a) $Fe\ (NH_2\ Trz)_3\ (BF_4^-)_2$
b) $Fe\ (NH_2\ Trz)_3\ Cl_2$
c) $Fe\ (NH_2\ Trz)_3\ (ClO_4^-)_2$
d) $Fe\ (NH_2\ Trz)_3\ (CO_3^{2-})$
e) $Fe\ (NH_2\ Trz)_3\ Br_2$ wherein $NH_2Trz$ is an amino-triazole ligand of the formula when R is an amino group.

7. A medium for storing, processing and/or displaying information as claimed in claim 4, wherein the metal-ligand complex is selected from the group consisting of triazole ligand complexes of Fe(II) having the general formulae a) $Fe\ (Trz)\ (Htrz)_2\ (BF_4^-)$
b) $Fe\ (H\ Trz)_2\ (NL_2\ Trz)\ Cl_2$
c) $Fe\ (H\ Trz)_2\ (NL_2\ Trz)\ (ClO_4^-)_2$
d) $Fe\ (H\ Trz)_2\ (NL_2\ Tr_3)\ (CO_3^{2-})$
e) $Fe\ (H\ Trz)_2\ (NL_2\ Trz)\ Br_2$
f) $Fe\ (Trz^-)\ (H\ Trz)\ (NL_2\ Trz)\ (BF_4^-)$
g) $Fe\ (Trz^-)\ (H\ Trz)\ (NL_2\ Trz)\ (Cl^-)$
h) $Fe\ (Trz^-)\ (H\ Trz)\ (NL_2\ Trz)\ (ClO_4^-)$
i) $Fe_2\ (Trz^-)_2\ (H\ Trz)_2\ (NL_2\ Trz)_2\ (CO_3^{2-})$
j) $Fe\ (Trz^-)\ (HTrz)\ (NL_2Trz)\ (Br^-)$
k) $Fe\ (Trz^-)\ (NL_2\ Trz)_2\ (Cl^-)$
l) $Fe\ (Trz^-)\ (NL_2Trz)_2\ (CLO_4^-)$
m) $Fe_2\ (Trz^-)_2(NL_2Trz)_4\ (CO_3^{2-})$
n) $Fe\ (Trz^-)\ (NL_2Trz)_2\ (Br^-)$
o) $Fe\ (RTrz)\ (NL_2Trz)_2\ (BF_4^-)_2$
p) $Fe\ (RTrz)\ (NL_2Trz)_2\ CL_2$
q) $Fe\ (RTrz)\ (NL_2Trz)_2\ (ClO_4^-)_2$
r) $Fe\ (RTrz)\ (NL_2Trz)_2\ (CO_3^{2-})$
s) $Fe\ (RTrz)\ (NL_2Trz)_2\ Br_2$.

8. A medium for storing, processing and/or displaying information as claimed in claim 4, wherein the metal-ligand complex is selected from the group consisting of triazole ligand complexes of Fe(II) having the general formulae a) $Fe\ (Trz^-)\ (H\ Trz)_2\ (BF_4^-)$
b) $Fe\ (Trz^-)\ (HTrz)_2\ (Cl^-)$
c) $Fe\ (Trz^-)\ (HTrz)_2\ (ClO_4^-)$
d) $Fe_2\ (Trz^-)_2\ (HTrz)_4\ (CO_3^{2-})$
e) $Fe\ (Trz^-)\ (HTrz)_2\ (Br^-)$
f) $Fe\ (RTrz)_3\ (BF_4^-)_2$
g) $Fe\ (RTrz)_3\ Cl_2$
h) $Fe\ (RTrz)_3\ (ClO_4^-)_2$
i) $Fe\ (RTrz)_3\ (CO_3^{3-})$
j) $Fe\ (RTz)_3\ Br_2$
k) $Fe\ (Trz^-)\ (RTrz)_2\ (BR_4^-)$
l) $Fe\ (Trz^-)\ (RTrz)_2\ (Cl^-)$
m) $Fe\ (Trz^-)\ (RTrz)_2\ (ClO_4^-)$
n) $Fe_2\ (Trz^-)_2\ (RTrz)_4\ (CO_3^{2-})$
o) $Fe\ (Trz^-)\ (RTrz)_2\ (Br^-)$
p) $Fe\ (HTrz)\ (NL_2\ Trz)_2\ (BF_4^-)_2$
q) $Fe\ (HTrz)\ (NL_2\ Trz)_2\ Cl_2$
r) $Fe\ (HTrz)\ (NL_2\ Trz)_2\ (ClO_4^-)_2$
s) $Fe\ (HTrz)\ (NL_2\ Trz)_2\ (CO_3^{2-})$
t) $Fe\ (HTrz)\ (NL_2\ Trz)_2\ Br_2$
u) $Fe\ (RTrz)_2\ (NL_2\ Trz)\ (BF_4)_2$
v) $Fe\ (RTz)_2\ (NL_2\ Trz)\ Cl_2$
w) $Fe\ (RTrz)_2\ (NL_2\ Trz)\ (ClO_4^-)_2$
x) $Fe\ (RTrz)_2\ (NL_2\ Trz)\ (CO_3^{2-})$
y) $Fe\ (RTrz)_2\ (NL_2\ Trz)\ Br_2$
z) $Fe\ (Trz^-)\ (RTrz)\ (NL_2\ Trz)\ (BF_4^-)$
aa) $Fe\ (Trz^-)\ (RTrz)\ (NL_2\ Trz)\ (Cl^-)$
bb) $Fe\ (Trz^-)\ (RTrz)\ (NL_2\ Trz)\ (ClO_4^-)$
cc) $Fe\ (Trz^-)\ (RTrz)\ (NL_2\ Trz)\ (CO_3^{2-})$
dd) $Fe\ (Trz^-)\ (RTrz)\ (NL_2\ Trz)\ (Br^-)$ in which R is selected from the group consisting of an alkyl group and $NL_2$, wherein L is H or an alkyl group, said medium being inscribable, eraseable and re-inscribable with data at ambient temperature.

9. A medium as claimed in claim 1, wherein the hygroscopic substance is selected from the group consisting of non-basic and weakly acidic hygroscopic soluble colorless salts comprising a $BF_4^-$, $ClO_4^-$, $CO_3^{2-}$, $Br^-$, and $Cl^-$ anion.

10. A medium as claimed in claim 9, wherein the hygroscopic substance is chosen from the group consisting of iron boron fluoride, magnesium perchlorate, potassium perchlorate, sodium perchlorate and mixtures thereof.

11. A medium as claimed in claim 1, wherein the metal-ligand complex comprises a mixture of said substituted triazole ligands.

12. A medium as claimed in claim 11, wherein the mixture of ligands comprises:

(a) a substituted triazole in which the radical R is H, an alkyl, and a free radical, and (b) an amino-triazole in which the radical R is an $NH_2$ group, and the amino-triazole is present in the mixture in a lesser amount than other ligands present in the metal-ligand complex.

13. A medium as claimed in claim 12, wherein the amino-triazole is present in the mixture of ligands in a molar ratio which is less than or equal to 1% of the total molar ratio of the other ligands.

14. A medium as claimed in claim 2 wherein the metal-liquid complex comprises metal-metal bonds.

15. A display device including as an active element a medium as claimed in claim 2.

16. A display device as claimed in claim 15 comprising a data display screen.

17. A display device as claimed in claim 15 comprising a coded addressing device.

18. A memory card including a data display device as claimed in claim 15.

19. A magic slate including a data display device as claimed in claim 15.

* * * * *